United States Patent

Faulder et al.

[19]

[11] Patent Number: 5,802,909
[45] Date of Patent: Sep. 8, 1998

[54] APPARATUS AND METHODS FOR MONITORING CARBON DISULPHIDE

[76] Inventors: George Charles Faulder, The Old Barn, Hollow Lane, Cheddleton, Leek, Staffordshire ST13 7HP; Richard Martin Faulder, Colour Mill Cottage, Winkhill, Near Leek, Staffordshire ST13 7PR; Roger Neil Bloor, Pinewood House, Pinewood Drive, Ashley Heath, Market Drayton, Shropshire TF9 4PA, all of United Kingdom

[21] Appl. No.: 793,466

[22] PCT Filed: Jun. 23, 1995

[86] PCT No.: PCT/GB95/01480

§ 371 Date: Feb. 26, 1997

§ 102(e) Date: Feb. 26, 1997

[87] PCT Pub. No.: WO96/00900

PCT Pub. Date: Jan. 11, 1996

[30] Foreign Application Priority Data

Jun. 28, 1994 [GB] United Kingdom ............... 9412909

[51] Int. Cl.$^6$ .................. G01N 33/497; G01N 33/00
[52] U.S. Cl. ................................ 73/23.3; 422/84
[58] Field of Search .................. 73/23.2, 23.3; 422/84; 436/900

[56] References Cited

U.S. PATENT DOCUMENTS 4,413,185  11/1983  Leveson et al. ............ 250/423 P

FOREIGN PATENT DOCUMENTS 62-151757  7/1987  Japan .
2 269 901  2/1994  United Kingdom .

OTHER PUBLICATIONS

S.O. Farwell et al., "Determination of Total Biogenic Sulfur Gases by Filter/Flash Vaporization/Flame Photometry", *Analytical Chemistry*, vol. 52, No. 14, Dec. 1980, Columbus, pp. 2370–2375.

*Primary Examiner*—Michael Brock
*Assistant Examiner*—Daniel S. Larkin
*Attorney, Agent, or Firm*—Young & Thompson

[57] ABSTRACT

An apparatus and an associated method for monitoring compliance with a disulfiram prescription regime. A self testing device 10 includes a gas sensor 12, a display 13, an indicating light 14, and a start button 15. An air inlet 16 is joined on the body 11 and a breath tube 12 can be located therein. A clock 20 in association with a random day generator 21 and the display 13, and light 14 determine the daily close rate and the measured sample is compared with expected sensor output by determining whether or not the user has complied with the regime.

6 Claims, 1 Drawing Sheet

APPARATUS AND METHODS FOR MONITORING CARBON DISULPHIDE

FIELD OF THE INVENTION

This invention relates to apparatus and methods for monitoring the level of carbon disuphide in a person's breath.

BACKGROUND OF THE INVENTION

It has been known for sometime that one method of attempting to maintain sobriety in alcoholics and other patients with drink problems is to prescribe a daily or regular dose of disulfiram, for example, as is sold under the Trade name ANTABUSE. This has the effect that if a patient were to take alcohol within 24 or 48 hours of the dose they would be extremely ill and it could even possibly be fatal. It is obviously important that the prescribing Doctor or agency can be certain that the dose prescribed is being taken both from the point of view of the success of the treatment, and also because compliance with the regime can frequently be a condition of continued employment for such patients. Employers usually require a report from the prescribing physician stating that, in his opinion, the prescribed doses have been taken as instructed. Currently, the only method of making this determination is by detailed interviewing of the patient and of his relatives and colleagues.

It has been known for sometime that patients who take disulfiram expire carbon disulphide in their breath. This has been measured on a laboratory basis with a view to determining whether or not a dose has been taken, but the methods and apparatus used have only been appropriate for a limited academic investigations.

Carbon disulphide is also a hazard in certain industries, such as the Rayon industry and, at present, there is no convenient apparatus or method for measuring exposure on an individual basis.

SUMMARY OF THE INVENTION

From a first aspect there is provided a breath testing apparatus having a sensor for detecting carbon disulphide.

From a second aspect the invention consists in an apparatus for self-testing for carbon disulphide in a sample of breath and means for storing the measurements on a daily basis.

It will be understood that by using a self-testing apparatus, the patient can build up a regular set of results which can be down loaded by the physician, who can check to see that the appropriate general level of carbon disulphide has been detected. In principle he could then immediately advise the employer or other agency the patient had complied with the regime. Conveniently, the self-tester may use a semiconductor or infra-red gas sensor for detecting the carbon disulphide and could be configured very much in the form of apparatus which is currently used for detecting breath alcohol. Theoretically, fuel cells may also be used but those which have currently been tested suffer from a very slow response time particularly after a number of measurement cycles have been completed. Improvements in fuel cell design may overcome these problems.

It is however, anticipated that there might be concern amongst the agencies or employers that such a self-tester could be defeated by one or more patients conspiring together.

Accordingly in a third aspect, therefore, the invention consists in an apparatus for monitoring compliance of a patient with a prescribed disulfiram regime, including means for obtaining a sample of a patient's breath, a gas sensor for detecting the level of carbon disulphide in the sample, and means for indicating variations in the dose regime to the patient in or immediately prior to the dose period of the varied dose.

Thus, if the patient had been instructed to take a single tablet at 10.00 a.m. each morning, the apparatus will indicate on at least one day in a dose cycle that half a tablet, or some other reduced dose, should be taken on that day and this will lead to a commensurate drop in the carbon disulphide. This will be detected when the following day's sample is given by the patient.

Because the patient has no significant prior warning of the day on which the reduced or altered dose will be taken, it would be very difficult for him to locate another patient who was following exactly the same pattern. It is preferred that the indicating means should determine the dose variation on a random basis, although the selection may not be entirely random, because it will usually be desirable to ensure that there is at least one reduced dose in any given prescribed period. It is also desirable that on occasion more than one reduced dose should occur so that patients cannot consider it is "safe" to avoid compliance once a reduced dose has been taken in a particular period.

The indicating means may include audible, tactile, and/or visual displays.

The apparatus may further include integral or separate means for comparing the detected level of carbon disulphide with an expected level for the regime period or a part thereof. Comparing means may produce an output signal indicating lack of compliance and this may generate a warning signal on the apparatus, so that the patient can return to the prescribing physician to have the apparatus cleared and himself put back on the intended regime.

From another aspect the invention consists in a method for determining compliance by a user with a disulfiram prescription regime, including self-monitoring on a regular basis of carbon disulphide in the breath of the user and comparing the test results with the anticipated results. The method may additionally include varying the dose regime at short notice and may be carried out using apparatus as defined above.

From a further aspect the invention includes a method of monitoring the carbon disulphide exposure of an individual including taking a breath sample from the individual and exposing it to a gas sensor for detecting carbon disulphide.

Although the invention has been defined above, it is to be understood it includes any inventive combination of the features set out above or in the following description.

BRIEF DESCRIPTION OF THE DRAWINGS

The invention may be performed in various ways and a specific embodiment will now be described, by way of example, with reference to the accompanying drawings, in which.

DETAILED DESCRIPTION OF THE INVENTION

Figure 1:
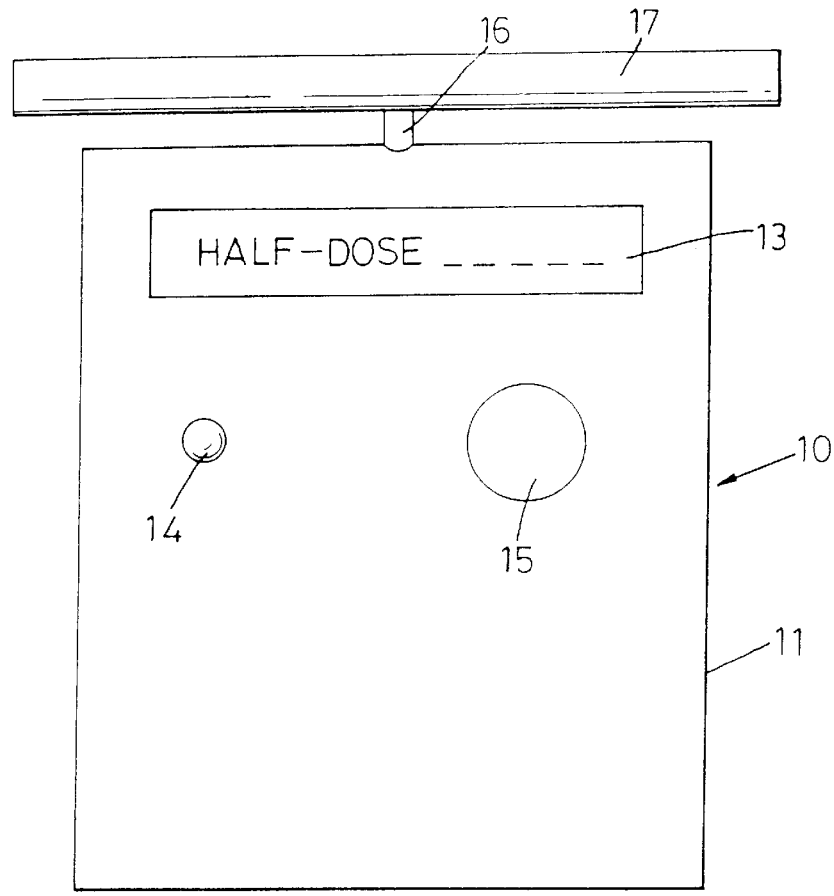
FIG. 1 is a diagrammatic view of self-testing apparatus.
Figure 2:
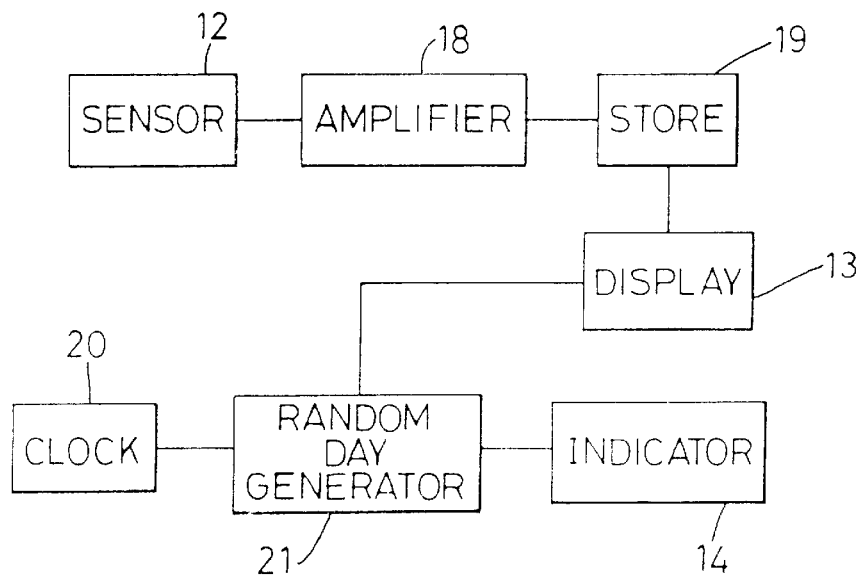
FIG. 2 is a circuit diagram of such apparatus.

A self-testing device is generally indicated at 10 in FIG. 1 and is very much in the form of a standard breath testing device. The device 10 comprises a body 11 which houses a semi-conductor gas sensor 12 and associated circuitry. The body 11 also has a display 13, an indicating light 14, and a start button 15. An air inlet 16 is formed on the body and a breath tube 17 can be located on the inlet.

As is well-known in the breath testing art, the user voids quantity of air through the tube 17 and the device 10 automatically takes a sample, via inlet 16, which is passed to the sensor 12.

In use, the sensor produces an output, which is amplified by an amplifier 18 and then stored in a memory or store 19. The reading may also be displayed on the display 13. The display 13 may give a value or may simply indicate that a valid dose has occurred. The store 19, may include a comparator means for detecting whether or not a signal is at the required level.

A real time clock 20 is connected to a random day generator 21 which is in turn connected to the display 13 and the indicator light 14. As has been explained above the generator can select a day in the prescription period and cause the words "HALF DOSE" or some other indication to appear on the display 13. The light 14 may also be illuminated and an audible alarm, (not shown) could sound.

It is preferred that the device 10 also has a data port through which the data held in the store can be down loaded into a main computer, which could then automatically generate a report showing compliance or non-compliance over the period of use. This port could also be used to set the "HALF DOSE" days in place of using the random day generator.

To ensure proper relationship between dosing and testing, the patients may be required to dose themselves at a particular time of day or within a particular period and they will be regarded as having failed to comply if they do not do so. If the patients are told to dose themselves immediately prior to giving the dose, they will then also have least warning of the "HALF DOSE" days.

The preferred gas sensor for a hand held device is a semi-conductor gas sensor such as the SP-AQ, SP11 and SP-12 sold by FIS Inc. These have the advantage of being relatively cheap and operating at high temperature so that any reactive products will be burnt off. Infra-red gas sensor may also be used particularly if significant accuracy is required. Fuel cells as has been mentioned above, are theoretically suitable but current designs have problems in practice.

We claim:

1. Apparatus for self-testing for carbon disulphide in a sample of breath comprising a gas sensor for detecting the carbon disulphide and generating a measure of carbon disulphide concentration in the sample and means for storing the measure on a daily basis.

2. Apparatus for monitoring compliance of a patient with a prescribed disulfiram regimen, comprising means for obtaining a sample of the patient's breath, a gas sensor for detecting the level of carbon disulphide in the sample, and means for indicating variations in the dose regimen to the patient in or immediately prior to the period in which the varied dose will be taken.

3. Apparatus as claimed in claim 2, wherein the indicating means varies the indicated dose on a random or quasirandom basis.

4. Apparatus as claimed in claim 2, further including integral or separate means for comparing the detected level of carbon disulphide with an expected level for the regimen period or a part thereof.

5. Apparatus as claimed in claim 4, wherein the comparing means produces an output signal indicating a lack of compliance.

6. A method for checking compliance with a disulfuram prescription regimen, which comprises self-monitoring, on a regular basis, of the level of carbon disulphide in a user's breath and comparing the test results with anticipated results and varying the dose regimen at short notice.

* * * * *